United States Patent [19]

Tanquary et al.

[11] Patent Number: 5,098,755
[45] Date of Patent: Mar. 24, 1992

[54] TEXTURED THERMOPLASTIC ELASTOMERIC FILM, ARTICLES COMPRISING SAME, AND METHOD OF MAKING SUCH TEXTURED THERMOPLASTIC ELASTOMERIC FILM AND ARTICLES

[76] Inventors: Albert C. Tanquary, P.O. Box 12885, Research Triangle Park, N.C. 27709; Robert G. Wheeler, 3818 S. Hwy. 525, Greenbank, Wash. 98253

[21] Appl. No.: 616,570

[22] Filed: Nov. 21, 1990

[51] Int. Cl.$^5$ .................. B21D 13/00; A61B 19/00; A61F 6/02

[52] U.S. Cl. .................. 428/35.5; 428/176; 428/156; 428/161; 604/347; 604/348; 604/349

[58] Field of Search .................. 428/156, 159, 35.5, 428/161, 36.9, 34.1, 36.8, 174, 176; 604/349, 347, 348

[56] References Cited

U.S. PATENT DOCUMENTS

| | | | |
|---|---|---|---|
| D. 253,009 | 9/1979 | Okamoto | D24/99 |
| 2,285,981 | 6/1942 | Johns . | |
| 2,586,674 | 2/1952 | Lunne | 128/294 |
| 4,574,156 | 3/1986 | Dyck et al. | 128/132 R |
| 4,798,600 | 1/1989 | Meadows | 604/347 |
| 4,964,416 | 10/1990 | Foldesy et al. . | |

FOREIGN PATENT DOCUMENTS

| | | |
|---|---|---|
| 0147072A1 | 3/1985 | European Pat. Off. . |
| 2085323 | 4/1970 | France . |
| 84297687 | 4/1983 | Japan . |
| 63-281965 | 11/1988 | Japan . |

Primary Examiner—James J. Seidleck
Assistant Examiner—Charles R. Nold

[57] ABSTRACT

Textured and embossed films are described which are usefully employed in the manufacture of condom articles. In one aspect, an elastic film is provided with an embossed pattern thereon comprising from about 1,000 to about 100,000 embossments per square inch of embossed surface. In another aspect, particularly advantageous in imparting extensibility characteristics to low elasticity or inelastic films, the film is textured with longitudinal and transverse fold lines defining respective longitudinal and transverse waveform profiles and comprising planar polygonal surface portions between and bounded by adjacent longitudinal parallel fold lines and adjacent transverse parallel fold lines, with from about 100 to about 100,000 polygonal surface portions per square inch of textured film surface. Corresponding methods for making such embossed and textured films are disclosed.

22 Claims, 9 Drawing Sheets

TEXTURED THERMOPLASTIC ELASTOMERIC FILM, ARTICLES COMPRISING SAME, AND METHOD OF MAKING SUCH TEXTURED THERMOPLASTIC ELASTOMERIC FILM AND ARTICLES

BACKGROUND OF THE INVENTION

1. Field of the Invention

This invention relates to textured film and articles made therefrom, and to a method of treating such film to enhance the elastic and/or extensibility characteristics thereof. In a specific embodiment, the invention relates to condom articles formed of thermoplastic elastomeric film which has been textured to enhance its elastic properties.

2. Description of the Related Art

In recent years, there has been a significant increase in the incidence and spread of sexually transmitted diseases (STD's). This phenomenon has in turn caused an increased use of condoms as a prophylactic measure to reduce the risk of infection and transmission of such diseases.

Among the reasons for the increase in incidence and rate of transmission of STD's are the development of increasingly antibiotic-resistant strains of disease-causing organisms, e.g., those responsible for diseases such as syphilis and gonorrhea. Another factor has been the absence of any effective cure for acquired immunodeficiency syndrome (AIDS).

The diseases with which AIDS has been or is suspected to be linked include Pneumocystis carinii pneumonia, Kaposi's sarcoma, esophageal or bronchopulmonary candidiasis, extrapulmonary cryptococcosis, cytomegalovirus internal organ infection, disseminated Mycobacterium avium complex or M. kansasii infection, chronic herpes simplex ulceration, chronic cryptosporidiosis enteritis, toxoplasmosis of the brain, high-grade B-cell non-Hodgkin's lymphoma, disseminated histoplasmosis, chronic isosporiasis enteritis, and lymphoid interstitial pneumonia in children.

Against the foregoing background, and the recognition that condoms afford a safe, low cost, and generally reliable means for combatting the spread of STD's, including AIDS, there has been an increased demand for condoms.

Currently, most condoms are produced from a latex resin via a dipping process in which a cylindrical and rounded-end mold is dipped into a resin bath, so that the mold is coated with a thin layer of the latex material. The thickness of the latex coating on the mold is dependent on the viscosity of the latex, and the speed of extracting the mold from the latex- bath. Similar latex dipping processes have been employed with suitably shaped molds to form tight-fitting gloves such as surgical gloves.

The above-described latex resin dipping process has been utilized for decades, and yields a generally satisfactory barrier product at reasonable cost.

With the recent spread of AIDS in the general population and the resurgence of condom usage in sexual activities, there has been interest in improving the strength and reliability characteristics of condoms, and of achieving improvements in manufacturing processes and economics, to further combat the spread of STD's generally, and AIDS specifically, as well as to provide a safe and reliable contraceptive means.

As indicated above, the thickness of conventional latex condoms is dependent on the viscosity of the latex in the mold dipping bath, and the speed of extraction of the mold from such bath. As a result of such viscosity and processing rate dependence, latex condoms generally are characterized by variations in thickness, which are usually acceptable, but which introduce variable material requirements into the manufacturing process.

Consideration has been given in the art to the possibility of using synthetic film materials for condom manufacture, to take advantage of mass production techniques and the high uniformity of thickness and material properties which are typical of most commodity polymeric films. In order to accommodate the requirement of relatively low thickness of the condom material, and the concomitant need for strength and stability in such material in order to maintain the structural integrity of the condom during its processing, storage, and subsequent use, attention has specifically been given to potential utilization of synthetic elastomeric polymer films as condom materials.

In respect of its physical properties, latex rubber has the advantage that it generally has a significantly lower modulus of elasticity as compared to synthetic elastomeric polymer films.

Nonetheless, synthetic elastomeric polymer films have significant potential advantages in use as a condom material of construction, particularly thermoplastic elastomeric materials, because of their ready formability, availability, and low cost, and their physical, chemical, and mechanical properties, including low porosity.

It therefore would be a significant advance in the art to provide a condom which is fabricated from a thermoplastic elastomeric material which exhibits the generally favorable properties of synthetic elastomeric films, but additionally is characterized by a reduced modulus of elasticity, such that the condom material more closely approximates the elastic properties and textural characteristics of natural latex rubber.

U.S. Pat. No. 4,574,156 issued Mar. 18, 1986 to Manfred F. Dyke discloses a condom formed of a thermoplastic polyurethane material, having a generally cylindrical configuration with an open proximal end and a closed distal end. The disclosed condom has a thickness of from about 0.01 millimeter, or less, to about 0.25 millimeter. The thermoplastic polyurethane employed to form the condom is disclosed as having: an average Shore A hardness of from about 50 to about 90; a tensile stress, at 100% elongation, between about 300 and 1,000 psi; and a tensile stress, at 300% elongation, between about 800 and 3,000 psi. Suitable thermoplastic polyurethane species for manufacturing the condom include those set out at column 2, line 55 to column 3, line 10 of the Dyke patent, with polyether- or polyester-based urethane elastomers said to be preferred. In the manufacture of the thermoplastic polyurethane condom disclosed in the Dyke patent, a film of the polyurethane material, e.g., in the form of a 6-inch square, is heated to a temperature high enough to soften the polymer but low enough to avoid chemical degradation, preferably in a clamping frame, and at a temperature of about 400°-500° F. The heated film then is brought into contact with a preformed mandrel to cause the film to assume the shape of the mandrel, preferably with application of a vacuum to the system in order to bring about uniformity in wall thickness (column 3, lines 47-50 of the patent).

European patent application 0 147 072 published July 3, 1985 in the names of Robert A. Taller, et al., discloses a process for making a polyurethane condom with a uniform thickness of from about 1.5 to about 4 mils. A heat-curable polyurethane prepolymer solvent solution is employed into which a mold is dipped and withdrawn for subsequent heat curing on the mold. The polyurethane prepolymer which is employed in the dipping medium is a prepolymer which is the reaction product of a polyisocyanate with at least one long-chain polyol. The polyol is amorphous at room temperature, has an average molecular weight of from about 500 to about 5,000, a hydroxy number of from about 225 to about 22.4, and an NCO/OH ratio of from about 0.95:1 to about 1.1:1.

U.S. Design Patent 253,009 to T. Okamoto shows a prophylactic device whose frontal (distal) section comprises a pair of indented surface portions forming circumferential grooves in the prophylactic, transverse to the longitudinal axis thereof.

U.S. Pat. No. 4,964,416 issued Oct. 23, 1990 in the names of Robin G. Foldesy and Robert G. Wheeler discloses a variety of condom configurations which are fabricated of thermoplastic materials such as thermoplastic elastomeric materials, and non-elastomeric materials such as olefinic homopolymers and copolymers, e.g., ultra-low-density polyethylene.

It therefore is an object of the present invention to provide films having enhanced elasticity and/or extensibility characteristics, such as may be usefully employed in the fabrication of condom articles.

It is another object of the invention to provide a method of treating a film material to enhance the elastic properties thereof and render it highly advantageous for applications such as condom articles.

Other objects and advantages of the present invention will be more fully apparent from the ensuing disclosure and appended claims.

SUMMARY OF THE INVENTION

In one aspect, the present invention relates to an elastomeric film having an embossed pattern thereon comprising a multiplicity of discrete embossments, with a pattern density of from about 1000 to about 100,000 embossments per square inch of embossed surface.

Another aspect of the invention relates to a condom comprising an elastomeric film as broadly described in the proceeding paragraph.

In still another aspect, the present invention relates to a textured film having longitudinal and transverse fold lines defining respective longitudinal and transverse waveform profiles and comprising planar polygonal (e.g., quadrilateral) surface portions between and bounded by adjacent longitudinal parallel fold lines and adjacent transverse parallel fold lines, with from about 100 to about 100,000 polygonal surface portions per square inch of textured film surface.

In yet another aspect, the present invention relates to a method of treating an elastomeric film to enhance the elastic properties thereof, comprising embossing the film with an embossment pattern comprising a multiplicity of discrete embossments with a pattern density of from about 1000 to about 100,000 embossments per square inch of embossment pattern surface.

In a preferred method aspect, the method described in the preceding paragraph is carried out by contacting a film of elastomeric material with a foraminous element under sufficient conditions of heat and/or pressure to emboss the film with the aforementioned embossment pattern.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
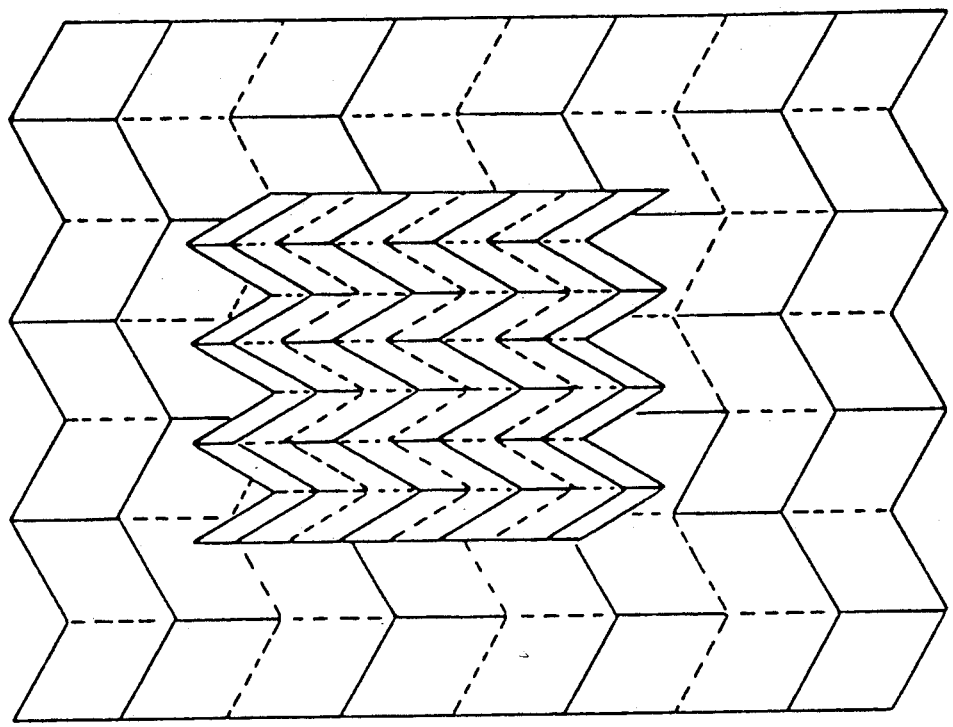
FIG. 1 is a plan view of a herringbone-patterned textured film formed of an inelastic material and accommodating biaxial extension, superimposed on a plan view of a corresponding film after it is stretched.

The present invention is based on the surprising and unexpected discovery that the elasticity and extensibility of film materials can be significantly improved by embossing or texturing of the film with an embossment or texturing pattern comprising pattern elements (pattern artifacts) having specific size/density characteristics on the film.

As used herein, "embossing" and "embossed" refer to the provision on the surface of an elastic or otherwise extensible film of an array of "embossments."

The term "embossments" as used herein refers to localized protrusions, convexities, concavities, asperities, or other localized deformations from the plane of a film or sheet material, i.e., the plane of the sheet or film when the sheet or film is in an untreated (unembossed) state and reposed on a flat support surface. Thus, the embossed elements or artifacts constitute discrete segments of the film or sheet which comprise deformations out of the plane of the film or sheet. Such embossments may be imparted to the film or sheet in any suitable manner, as hereinafter more fully described.

As used herein, the terms "heat-treating" and "heat-treated" refer to subjecting a film or sheet material to elevated temperature conditions, below temperature levels which would cause deterioration or degradation of such material, and with such elevated temperature treatment including processing at ambient pressures as well as at elevated pressure (e.g., compression, tension, or expansion) or sub-ambient pressure conditions.

The term "virgin" as used herein refers to a film or sheet material which has not been heat-treated (except for stabilization aging, such as is carried out for some film materials subsequent to film formation at relatively low temperature, e.g., about 50° C. or less) and/or embossed. It will be understood that embossing as referred to herein will invariably involve subjecting the film or sheet to some sort of pressure (tension, compression, expansion, etc.) conditions, though the invention is also potentially applicable to any embossment methods which can be carried out at ambient or other (vacuum or subatmospheric) pressure levels. Embossing in any event will be carried out under suitable heat and/or pressure conditions as requisite to impart the desired embossment pattern to the film or sheet, in the broad practice of the present invention.

The film and sheet materials which may be embossed or otherwise textured in accordance with the present invention include any suitable materials susceptible to manufacture of thin (e.g., less than 300 mils) flexible webs to which embossment or texturing patterns of the present invention can be imparted, to enhance the elastic or extensibility characteristics thereof. Thus, the invention is potentially applicable to a wide variety of materials such as metal foils, paper, composite sheet materials, polymeric films, and natural and synthetic membranes, etc. Polymeric films are particularly preferred in the practice of the invention as an embossment or texturing medium, and thermoplastic materials are especially preferred, including elastomeric thermoplastic materials, as well as non-elastomeric materials such as olefinic homopolymers and copolymers, e.g., ultra-low density polyethylene.

As used herein, the terms "elastic" and "elastomeric" in reference to films and sheets in accordance with the present invention, mean a film or sheet which subsequent to elongation thereof under an applied tensional force, regains at least a significant portion of its original dimensional characteristics when the applied tensional force is released.

As used herein, the term "textured" refers to film and sheet materials which comprise surface deformations (relative to a planar untextured film or sheet) including embossments as well as multiple surface regions or faces produced by uniaxial or biaxial folding, shaping, or the like, whereby the so-treated film or sheet is rendered more elastic or extensible in character.

Illustrative of thermoplastic elastomeric materials which may find utility in the broad practice of the present invention are: polyurethane materials, as for example the polyester-based polyurethane material commercially available from Mobay Company (Plastics and Rubber Division, Pittsburgh, Pa.) under the trademark Texin ®, and the thermoplastic polyurethane elastomers which are commercially available from Atochem, Inc. (Glennrock, N.J.) under the trademark Platilon ® and the thermoplastic polyurethane elastomers from polyurethane resins which are commercially available from BASF Corporation (Parsippany, N.J.) under the trademark Elastollan ®; polyester elastomers, such as the block copolymers of polybutylene terephthalate and long-chain polyether glycols, which are available commercially from E.I. DuPont de Nemours and Company, Inc. (Polymer Products Department, Engineering Polymers Division, Wilmington, Del.) under the trademark HYTREL ®; polyether blockamides, such as those commercially available from Atochem, Inc. (Glennrock, N.J.) under the trademark Pebax ®; multiblock rubber-based copolymers, particularly those in which the rubber block component is based on butadiene, isoprene, or ethylene/butylene, such as the multiblock rubber-based copolymers commercially available from Shell Chemical Company (Houston, Tex.) under the trademark Kraton ®; ethylene-octene copolymers such as those commercially available from The Dow Chemical eCompany (Midland, Mich.) under the trademark ATTANE TM; as well as any other suitable homopolymers and copolymers, and mixtures, alloys, laminates, and composites thereof.

Among the foregoing materials, polyether- and polyester-based polyurethanes, and multiblock rubber-based copolymers, are most particularly preferred. The most preferred thermoplastic materials useful in condom articles according to the present invention are the aforementioned thermoplastic polyurethane elastomers whose resins and films are commercially available under the trademarks Elastollan ® and Platilon ®, respectively.

In application of embossments or textures to webs of multiblock rubber-based copolymers in the practice of the present invention, it will be understood that the non-rubber repeating units of the copolymer may be derived from any suitable monomer(s), e.g., (meth)acrylate esters, such as methyl methacrylate, cyclohexlymethacrylate, etc.; vinyl arylenes, such as styrene; etc.

In general, the non-rubber blocks in such multiblock rubber-based copolymers preferably are derived from monomer(s) which are non-elastomeric in character, so that "soft" rubber blocks and "hard" non-elastomeric blocks are provided in the multiblock copolymer. Such hard blocks may suitably be derived from monomers having a glass transition temperature ($T_g$) of at least about 50° C., with styrene being generally preferred. The rubber block of such multiblock copolymers may be formed of repeating units derived from synthetic rubbers such as butadiene, isoprene, ethylene/butylene, etc., with butadiene and ethylene elastomeric blocks generally being preferred.

Other rubber-based polymeric materials which may be employed as materials of construction in the broad practice of the present invention include rubber-based polyurethane materials, such as are prepared from polybutadiene diol-based thermoplastic urethane polymers.

The most preferred multiblock rubber-based copolymers for use in the broad practice of the present invention are those having an A-B-A structure comprising polystyrene endblocks and an elastomeric midblock. Illustrative multiblock butadiene-based copolymers which may be usefully employed in the practice of the present invention include those variously described in U.S. Pat. Nos. 3,297,793; 3,595,942; 3,402,159; 3,842,029; and 3,694,523, the disclosures of which hereby are incorporated by reference herein. Various multiblock butadiene-styrene copolymers may be usefully employed, such as the aforementioned triblock ethylene-butadiene-styrene copolymers commercially available under the trademark Kraton® from Shell Chemical Company (Houston, Tex.) and small block butadiene-styrene copolymers commercialized by Firestone Synthetic Rubber & Latex Company (Akron, Ohio) under the trademark Stereon®.

In the general use of a multiblock rubber-based copolymer as the material of construction for the embossed or textured articles of the present invention, the copolymer material preferably is characterized by the following physical properties: a Shore A hardness of from about 25 to about 100; a tensile strength of from about 500 to about 4500; a 300% modulus of from about 120 to about 1,000 psi; and an ultimate elongation of from about 200 to about 1400%.

With reference to the use of polyurethanes as materials of construction for the embossed or textured articles of the present invention, preferred material characteristics include: a specific gravity of from about 1.00 to about 1.25, a Shore A hardness from about 60 to about 100, a tensile strength from about 4500 to about 6,000 psi; a tensile stress at 50% elongation of from about 300 to about 2400 psi, an ultimate elongation of from about 350% to about 600%, a flexural modulus of from about 3,000 to about 37,000 psi, and a tear strength of from about 400 to about 1,000 pli.

In one aspect, the present invention relates to an elastomeric film having an embossed pattern thereon comprising a multiplicity of discrete embossments, with a pattern density of from about 1000 to about 100,000 embossments per square inch of embossed surface.

Preferably, the elastomeric film comprises a thermoplastic elastomeric film of suitable thickness. Preferably, the thickness of the elastomeric film does not exceed about 100 mils, more preferably about 40 mils, and a suitable thickness in the case of polymeric elastomeric films in applications such as condom articles, in which film thickness is an important consideration, is generally on the order of 1-10 mils to accommodate the competing considerations of strength and structural integrity, on the one hand, and thinness for heat transfer and physical pleasure on the other hand.

It has been found that an elastomeric film embossed with a pattern having the previously described pattern density characteristics has improved elastic properties, including a reduced elastic modulus and concomitantly improved stretching and tactile ("hand") qualities, as will be more quantitatively illustrated hereinafter. While we do not wish to be bound by any theory or hypothesis as regards the improvement in physical properties achieved by the practice of the present invention, it may be that the embossment involves or is associated with stretching or other stress-induced deformation in the embossing process which results in stress softening of the elastomeric film, yielding the improved physical properties. Thus, the elastomeric film may be subjected to elevated temperature and/or pressure conditions which may effect stress softening of the film to improve its textural and physical property characteristics.

In a preferred aspect, in application to elastomeric films employed for the manufacture of condom articles, the embossment pattern density preferably is from about 2000 to about 50,000 embossments per square inch of embossed surface, more preferably from about 5,000 to about 40,000 embossments per square inch of embossed surface, and most preferably from about 10,000 to about 30,000 embossments per square inch of embossed surface.

As indicated hereinabove, a preferred material in the broad practice of the present invention, particularly in application to the manufacture of condom articles, is polyurethane film, especially polyether-based polyurethane film.

The embossing of elastomeric films in accordance with the present invention may be carried out in any suitable manner, and preferably is carried out by imparting a pattern of the desired character to the elastomeric film with the use of elevated heat and/or pressure conditions. In preferred practice, a patterned element, or foraminous element, e.g., a mesh or screen member, is contacted with the elastomeric film at elevated heat and/or pressure conditions to impart a corresponding embossment pattern to the film. For example, the foraminous member may be employed in combination with a flexible resilient opposing member which is matable with the elastomeric film or other web material therebetween. In such instance, the foraminous member preferably is relatively more rigid and harder, as compared to the member matable therewith which is relatively softer, more deformable, and more resilient in character, to enhance the impartation of the embossment or textural pattern to the web being treated. In instances where the foraminous member is a screen or mesh element, the relatively softer "backing" member matable therewith may be formed of a material such as a 50 to 100-durometer-hardness material, e.g., a rubber or other elastomeric material.

The embossments utilized in embossed films and sheets according to the present invention may have any suitable shape, although such pattern elements preferably are of a geometrically regular shape. The embossment pattern may comprise a multiplicity of different constituent embossment shapes and/or size, in a regular or random array with respect to each other, but it generally is preferred for ease of manufacturing to utilize embossment elements which are all of a similar shape and configuration.

For example, the embossments may have a triangular shape, or a quadrilateral shape, e.g., a rectangular shape, or other polygonal shape, or may be of circular or other regular or irregular shape.

In the practice of the invention wherein a thermoplastic elastomeric film is employed as the embossment medium, and the embossing is carried out at elevated temperature, the temperatures employed with commercially available thermoplastic elastomeric films typically are at least 200° F and are below the degradation or decomposition temperature of the thermoplastic elastomeric film material. The embossment may be carried out at any specific temperature, and for any suitable time, e.g., from 1-60 seconds, or even longer, to impart the requisite embossment pattern to the elastomeric film.

In the case of a polyurethane film, such as the aforementioned polyester-based or polyether-based films, the embossment conditions may suitably include temperatures on the order of from about 200° F. to about 350° F., an elevated pressure of from about 100 psi to about 500 psi, and a duration of about 2-60 seconds duration in the embossing operation, when a screen or mesh member is employed as the foraminous element for embossing the film. In general, any suitable temperature, pressure, and time conditions may be employed, as appropriate to the specific material being embossed, and depending on its thickness, and the specific embossment means employed.

In the case of films of block copolymers being embossed, such as the ethylene-butadiene-styrene copolymers commercially available under the trademark Kraton ®, the embossing conditions may suitably include a temperature of from about 150° F. to about 200° F., a pressure of from about 50 to about 100 psi, and an embossing time of from about 2 to about 100 seconds.

The embossed or textured web materials of the present invention may be utilized in any applications in which corresponding unembossed on untextured webs are employed, including products in which a thin, flexible, imperforate material is advantageously employed, as for example, condoms surgical gloves, diapers, shower caps, dental dams, surgical drapes, gaskets, fluid-tight cuffs, and collars, surgical implants, wound dressings, and the like. In a particularly advantageous application of embossed films according to the present invention, a condom is constructed of a suitable thermoplastic elastomeric film comprising the embossed film, as hereinafter more fully described.

The foregoing description has been directed primarily to elastic and elastomeric web applications of the present invention. However, the present invention also comprehends textured films which are comprised of web materials having low elasticity, e.g., cellulosic webs, and the like. In such aspect of the invention, a textured film or sheet is provided which is folded to yield a web article of extensible character. Although accordion-folded structures of cellulosic materials, e.g., handheld fans, as known, there has not been to our knowledge any biaxially folded web structures which have the dimensional and geometric characteristics of the textured film or sheet articles of the invention, as described below.

In the folded web embodiment of the invention, which represents an alternative to embossment, a sheet or film of suitable material is textured by provision therein of longitudinal and transverse fold lines. These fold lines define respective longitudinal and transverse waveform profiles, with planar polygonal surface portions between and bounded by adjacent longitudinal parallel fold lines and adjacent transverse fold lines, and with from about 100 to about 100,000 polygonal surface portions per square inch of textured film surface. Preferably, the polygonal surface portions are quadrilateral, e.g., rectangular or parallellogramic, in shape. In one embodiment, described more fully hereinafter, the textured film or sheet fold lines define a herringbone pattern. The waveform pattern produced by the longitudinal and transverse fold lines may be any suitable wave form shape, as for example sawtooth waveform and sinusoidal waveform shapes.

The longitudinally/transversely folded film or sheet of the invention may be formed of any suitable material, including those illustratively described hereinabove with respect to embossed embodiments of the invention. However, the folded embodiment is particularly suited to the use of materials having low elasticity or an inelastic character, whereby these materials are rendered extensible in character. By such textural folding, webs of low extensibility or inelastic character are made adaptable to usages in which the textured sheet or film is subjected to stretching, and pulling, as well as other translational, torsional, and deformational forces, which would otherwise cause the web to lose its structural integrity in the absence of such textural folding.

With respect to the embossment of elastic films in the preferred practice of the invention, for usage in applications such as the manufacture of condom articles, it is preferred that the embossment pattern density and embossment configuration (size, shape and arrangement of embossments) be such that the modulus of elasticity of the embossed article is significantly less than the modulus of elasticity of the unembossed film.

In the case of a thermoplastic elastomeric material, it generally is preferred that the elastic modulus at 10% elongation ($M_{10}$) and 20% elongation ($M_{20}$) be at least 30% less than the $M_{10}$ and $M_{20}$ values for the corresponding unembossed film, and that the modulus of elasticity at 50% elongation ($M_{50}$) be at least 20% less than the $M_{50}$ value for the corresponding unembossed film.

It is also desirable, particularly in the case of thermoplastic elastomeric materials for applications such as condoms, where stresses are applied to the film in the use of the final product, for the embossment pattern and embossment element configuration to be selected to increase the tensile strength of the film by the embossment, relative to the tensile strength of the corresponding unembossed film. In the case of thermoplastic elastomeric materials, such as polyurethane, used in the manufacture of condom articles in accordance with the invention, the tensile strength measured by the method of ASTM D412 suitably is at least 10% greater than the tensile strength value measured by such method for the corresponding unembossed film.

As discussed hereinabove, the embossment pattern may be applied to an elastic film in the broad practice of the present invention by any suitable method and means. For example, a foraminous member such as a screen or mesh element may be contacted with the elastic film under conditions of heat and/or pressure, to deformingly impart to the elastic film the desired embossment pattern. Alternatively, the embossments may be applied to the elastic film by a heated pattern roll assembly in which at least one of the rolls is suitably engraved or textured to impart the desired embossment pattern to the film. For example, the film may be passed through a nip roll arrangement comprising a textured roll, and an untextured, resilient facing roll cooperating with the textured roll, to impart the desired embossments to thermoplastic elastomeric film passed therethrough.

Alternatively, the embossment pattern could be imparted to the elastic film by an opposed array of microjets of fluid impinged on opposite faces of a film or sheet of material so as to deformingly impart the desired involutions, protrusions, or other embossments to the film. It will be appreciated that the manner and means of embossing the sheet or film material in the broad practice of the present invention may be widely varied depending on the specific material of construction of the sheet or film, its thickness, and its physical, chemical, and mechanical properties.

In like manner, the method of imparting fold lines to a web to provide a biaxially extensible sheet or film material, may be correspondingly varied, and may involve contacting the sheet or film to be textured with a correspondingly configured die, roll, hot pressing element, etc.

In application to elastic web elements, the methodology of the present invention has been found to produce sheet or film articles of substantially improved elastic and tensile strength characteristics. Accordingly, articles which have been embossed or textured in accordance with the present invention are thereby rendered more suitable for use in applications where the sheet or film is subjected to stresses, pressures, and/or other deforming forces which in the absence of embossment or texturing would cause injury to or adversely affect the web and product articles comprising same.

Referring now to the drawings, FIG. 1 is a plan view of a herringbone textured film formed of an inelastic material and accommodating biaxial stretching thereof, superimposed on a plan view of the corresponding film in its extended (unfolded) condition. In this drawing, solid lines demarcate the film edges and upward (convex) folds, while broken lines represent downward (concave) folds. By means of this texturing of the film, a flat film can be converted to a textured film having the capability for lateral, as well as longitudinal, extensibility, without damage to or destruction of the web.

This pattern responds uniquely to stretching in one direction by becoming wider instead of narrower in the transverse direction. This property sometimes is referred to as a Poissons Ratio. For example, inserting a large diameter finger in a herringbone textured glove would cause the glove finger to become longer. Thus the herringbone pattern may be employed to impart a negative Poissons Ratio to the film textured thereby.

In the textured film shown in FIG. 1, the film has longitudinal and transverse fold lines defining respective longitudinal and transverse waveform profiles of sawtooth configuration, which form planar quadrilateral (parallellogramic) portions between and bounded by adjacent longitudinal parallel fold lines and adjacent transverse parallel fold lines. As an alternative to the sawtooth waveform configuration provided in the FIG. 1 web, the web may be folded or otherwise deformed to provide other waveform configurations, e.g., sinusoidal waveform shapes.

The FIG. 1 web desirably comprises from about 100 to about 100,000 quadrilateral (parallellogramic) surface portions per square inch of textured film surface. By this very fine folding, a structure is produced which affords a high degree of compaction and extensibility of the web, between the folded and unfolded conformations thereof, as is illustrated by FIG. 1.

Figure 2:
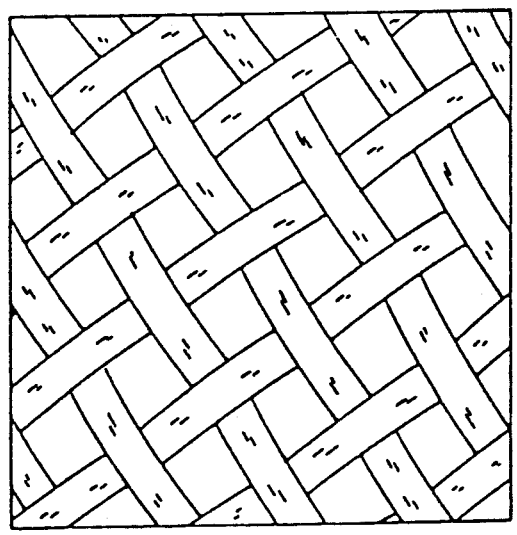
FIG. 2 is a schematic drawing of a scanning electron micrograph of 120-mesh screen that may be used to produce an embossed film according to the invention
Figure 3:
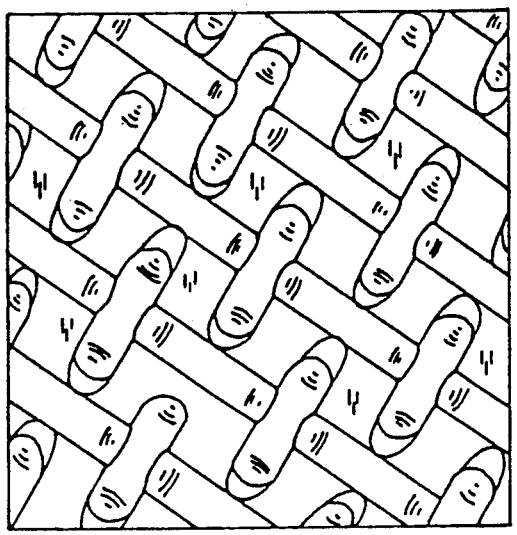
FIG. 3 is a schematic drawing of a scanning electron micrograph of the embossments on a 0.04-mm thick polyurethane film embossed with a 120-mesh screen according to the invention.
Figure 4:
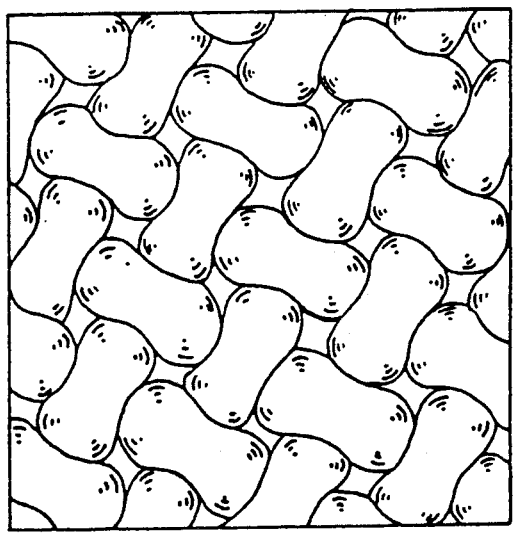
FIG. 4 is a schematic drawing of a scanning electron micrograph of the reverse side of the embossed film shown in FIG. 3.

FIG. 2 is a schematic drawing of a scanning electron micrograph of a 120 mesh screen which is employed to form the embossed film whose respective sides are shown in FIGS. 3 and 4. The advantage of using mesh or screen elements of such type as the embossment member is that same are readily commercially available in a wide range of mesh sizes. As used herein, the term "mesh size" is the number of holes or openings per linear inch. Thus, for example, a mesh or screen having a 15 mesh size has 15 openings per lineal inch both in the longitudinal and transverse directions of the screen or mesh, and 225 ($15 \times 15$) openings per square inch. While the mesh sizes of foraminous elements may be widely varied in their use as embossing means, in preferred practice, thermoplastic elastomeric films, e.g., polyurethane thin film (1-20 mil thickness), have been satisfactorily embossed with screens having a mesh size of from about 30 mesh to 300 mesh, and more preferably from about 100 to about 200 mesh.

The screen element whose structure is depicted in FIG. 2 preferably is used in combination with a resilient facing element, so that the elastic film may be positioned therebetween and subjected to compressive contact between the respective screen and backing elements, under elevated temperature conditions. In such manner, the film has imparted to it a heat-embossed pattern corresponding to the mesh structure of the screen, as depicted in FIGS. 3 and 4.

The facing element cooperating with the screen element in the embossing operation may be relatively soft and compressible, or may be suitably contoured relative to the mesh, so that a film pressed between the screen and backing elements will be of uniform thickness. It is preferred in the embossing operation to utilize the mesh in combination with a facing element of such type, so that the embossed film will be relatively uniform in thickness.

As the mesh size of the embossing screen element decreases, the hardness of the facing surface element preferably decreases to facilitate effective embossment of the film. Although the hardness of the facing element in such embossment systems may be varied widely, depending on the characteristics of the film and processing system, it has generally been found suitable to utilize a facing member with a hardness of from about 50 to about 100 durometer hardness, when embossing thermoplastic elastomeric films, e.g., of polyurethane, with screen elements of the mesh sizes described hereinabove. For example, with a screen element having a mesh size of from about 100 to about 150, a facing element with a hardness of about 60 durometer has been found effective to provide advantageous embossment of the polymeric film.

FIGS. 3 and 4 are schematic drawings of scanning electron micrographs of the embossment (screen-contacted) side (FIG. 3) and the reverse side (FIG. 4) of a 0.04 millimeter (mm) Elastollan ® polyurethane film embossed with a 120 mesh screen.

By embossment, a corresponding embossed pattern is imparted to the polyurethane film. In the broad practice of the present invention, the embossed pattern comprises a multiplicity of discrete embossments (embossment pattern elements, or embossment pattern artifacts), at a pattern density of from about 1000 to about 100,000 embossments per square inch of embossed surface, preferably from about 2000 to about 50,000 embossments per square inch, more preferably from about 5,000 to about 40,000 embossments per square inch, and most preferably from about 10,000 to about 30,000 embossments per square inch.

Analysis of heat-embossed films in accordance with the present invention reveals that elevated temperature conditions in the embossing operation account for some of the decreased modulus and improved elastic and other physical properties of the film, however, such characteristics of the film are further and substantially enhanced by the film embossments per se.

The features and advantages of the present invention are more fully illustrated by reference to the following non-limiting examples.

EXAMPLE I

Figure 18:
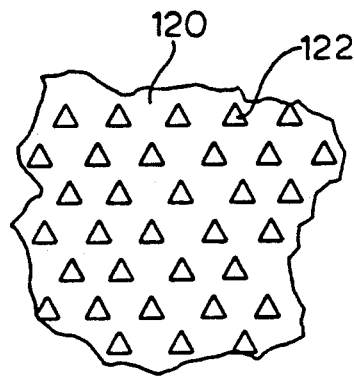
FIG. 18 is an enlarged view of a portion of an embossed thermoplastic elastomeric film having embossments of triangular shape.

Elastomeric polyurethane films approximately 35 micrometers in thickness were embossed with a pattern of triangular protrusions to provide a pattern of the type shown in FIG. 18 hereof. The polyurethane film material was Elastollan ® 1185-A (BASF Corporation, Parsippany, New Jersey). Texturing was carried out by photoengraving the desired pattern on a stainless steel plate. The triangular element pattern then was transferred to the thermoplastic film by hot pressing.

A textured and a corresponding non-textured strip of the polymeric film were joined to one another at respective ends by heat sealing, so that they could be strained in series with respect to one another. The strain characteristics of an initial 2 centimeter portion of each joined strip was measured with a dial caliper at various total elongation levels for the joined (textured and non-textured) specimens. The results are shown in Table I below.

These data show that the loading required to impart a given strain to the film was substantially greater for the untextured sample than for the textured sample. Conversely, the strain imparted to the textured sample at a given loading (stress level) was significantly greater than the strain exhibited by the corresponding untextured sample.

TABLE I

| Stretch (cm) | TEXTURED Load (g) | TEXTURED Stress (MPa) | Both % Strain | UNTEXTURED Load (g) | UNTEXTURED Stress (MPa) |
|---|---|---|---|---|---|
| 0. | 0 | 0 | 0.000 | 0 | 0.00 |
| 0.5 | 70 | 0.88 | 14.286 | 140 | 2.20 |
| 1 | 133 | 1.67 | 28.571 | 270 | 3.80 |
| 1.5 | 193 | 2.42 | 42.857 | 350 | 4.80 |
| 2 | 257 | 3.21 | 57.143 | 400 | 5.50 |
| 2.5 | 303 | 3.79 | 71.429 | 450 | 6.20 |
| 3 | 340 | 4.25 | 85.714 | 480 | 6.60 |
| 3.5 | 370 | 4.63 | 100.000 | 490 | 6.90 |
| 4 | 400 | 5.00 | 114.286 | 500 | 7.20 |
| 4.5 | 433 | 5.42 | 128.571 | 520 | 7.40 |
| 5 | 467 | 5.83 | 142.857 | 570 | 7.70 |
| 5.5 | 497 | 6.21 | 157.143 | 580 | 8.00 |
| 6 | 517 | 6.46 | 171.429 | 610 | 8.30 |
| 6.5 | 543 | 6.79 | 185.714 | 600 | 8.50 |
| 7 | 573 | 7.17 | 200.000 | 620 | 8.70 |
| 7.5 | 597 | 7.46 | 214.286 | 630 | 9.00 |
| 8 | 603 | 7.54 | 228.571 | 670 | 9.20 |

EXAMPLE II

Polyester polyurethane, PLATILON ® UO-73 produced by BASF Corporation (Parsippanny, N.J.), was obtained from Atochem, Inc. (Glen Rock, N.J.) as a film which was coextrusion blown with polyethylene and had a thickness of 50 microns. The polyethylene carrier film was removed prior to the tests described below.

The PLATILON ® film then was embossed by placing the film between a 150 mesh stainless steel screen (architectural screen made of a stainless steel wire cloth, as obtained from Gretchen Bellinger (New York, N.Y.)) and a 60 durometer rubber sheet, and pressing the film at 250° F. for 1 minute at 300–400 psi.

Heat-treated samples of the PLATILON ® film were used as a control, and were prepared by the same procedure as employed for the embossed samples but without the 150 mesh screen being used in the pressing step. Untreated (virgin) PLATILON ® film was used as a second control.

Circular rings of respective virgin, heat-treated, and embossed samples of the PLATILON ® film were prepared from a 16 cm wide strip of film that was folded and heat-sealed at its ends, and then cut into circular strips 1 cm wide with a circumference of 16 cm.

Each circular ring of PLATILON ® film then was hung over a 1/16-inch diameter pin. Weights consisting of tubular containers holding measured amounts of lead birdshot and fitted with bails at their open ends then were mounted on the rings, with the bails being passed through the ring specimens and then snapped into two diametrically opposite holes at the rim of the tubular weight. In this manner, the weight was freely suspended by two thicknesses of film whose length was ½ the circumference of the ring.

Three sets of eight weights (one set for each of the respective embossed, heat-treated, and virgin samples) ranging from 160 gm to 1024 gm, in 180 gm increments, were used. Testing was done at ambient temperature conditions (65°±8° F.).

Figure 5:
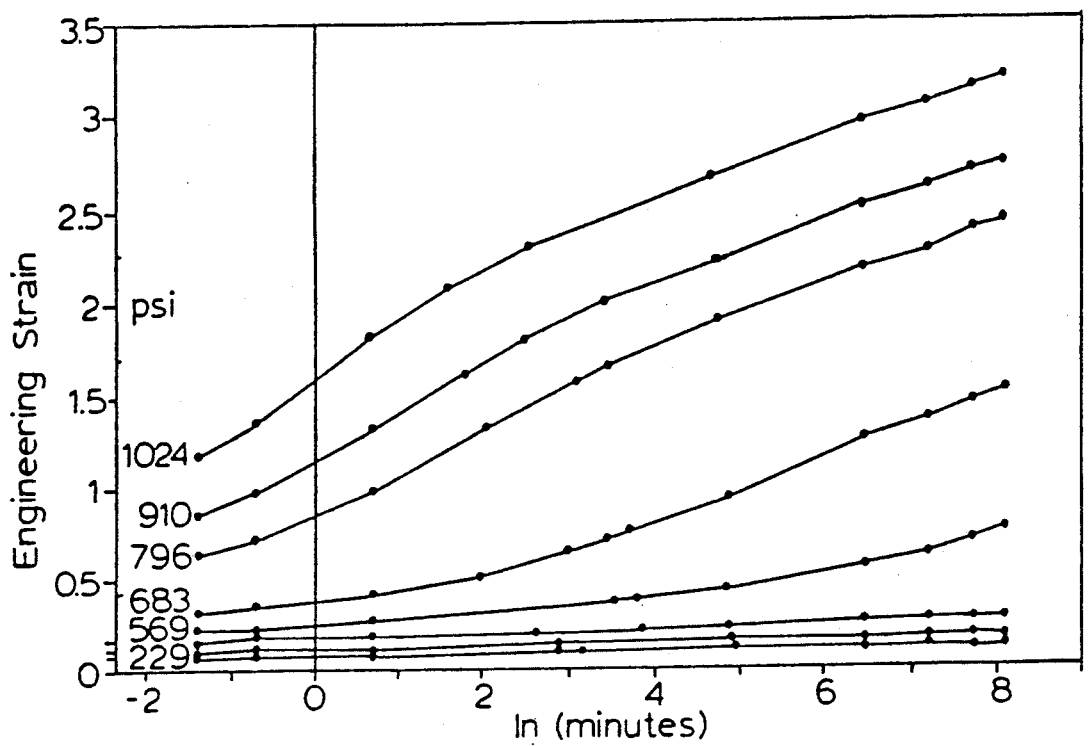
FIG. 5 is a semi-log plot of the engineering strain of virgin Platilon ® film as a function of time, at various load levels.
Figure 6:
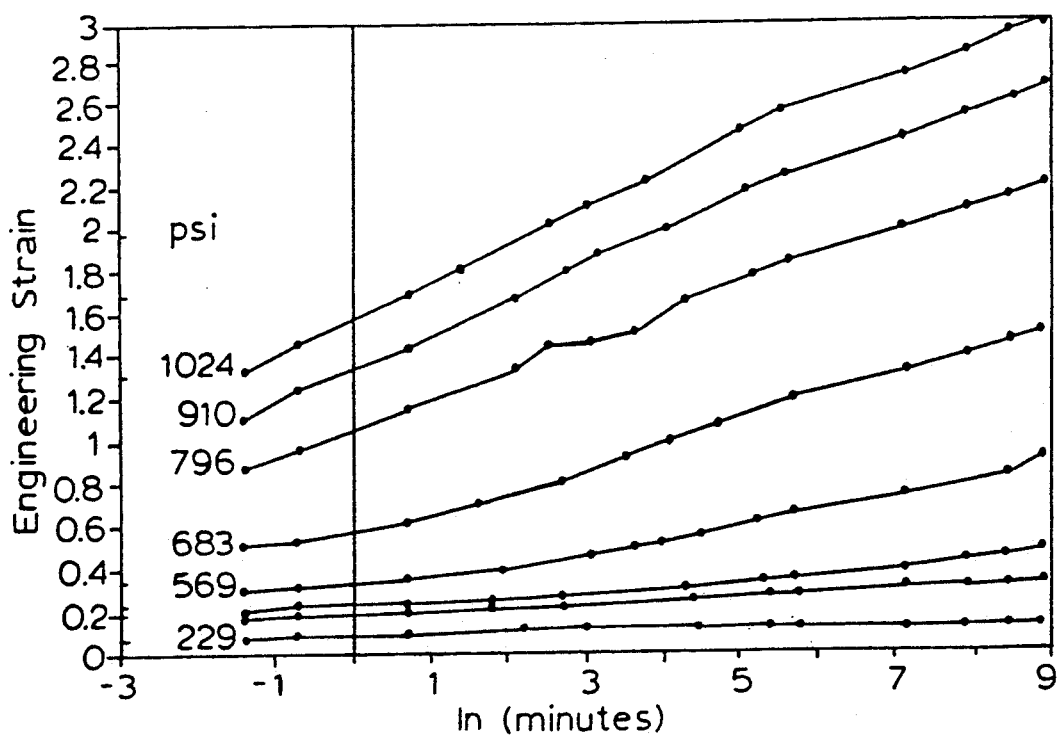
FIG. 6 is a semi-log plot of the engineering strain of an embossed Platilon ® film as a function of time, at various load levels.
Figure 7:
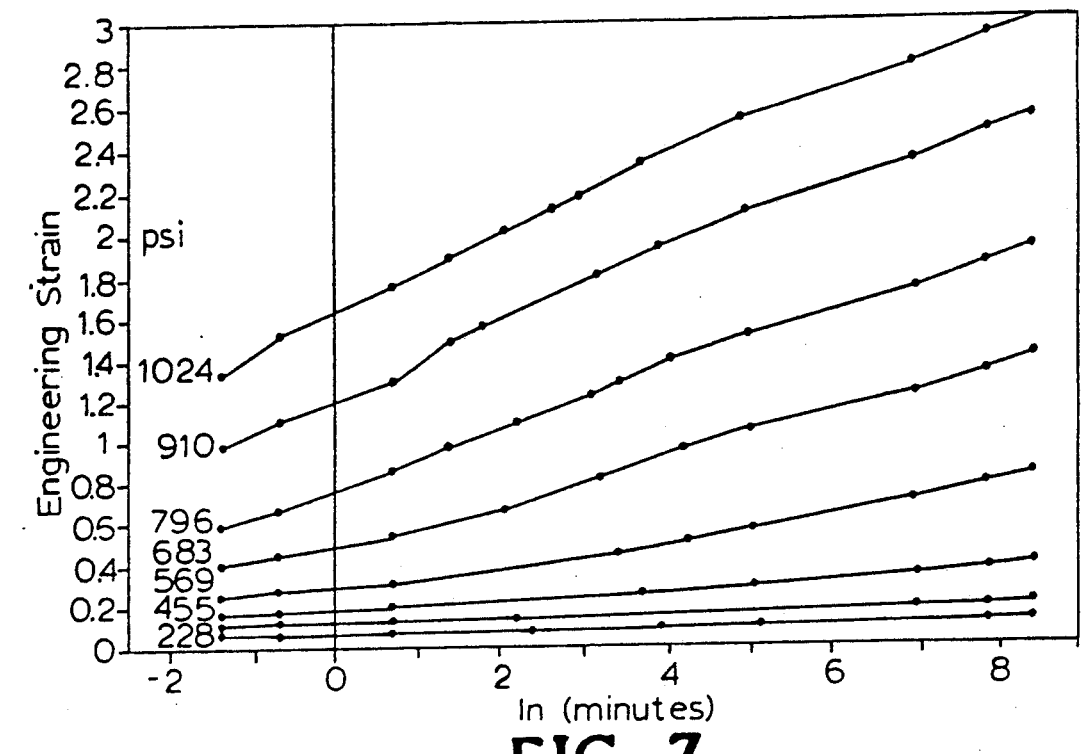
FIG. 7 is a semi-log plot of engineering strain of a heat-treated Platilon ® film as a function of time, at various load levels.

The data from these tests were plotted and the resulting graphs are shown in FIGS. 5–7, in which engineering strain is plotted as a function of the natural logarithm (ln) of loading time (minutes), for eight loading levels.

FIG. 5 is the semi-log plot of strain as a function of time at various selected loading levels, for virgin PLATILON ® film, while FIGS. 6 and 7 are the corresponding plots for embossed PLATILON ® film (FIG. 6) and heat-treated PLATILON ® film (FIG. 7).

Figure 8:
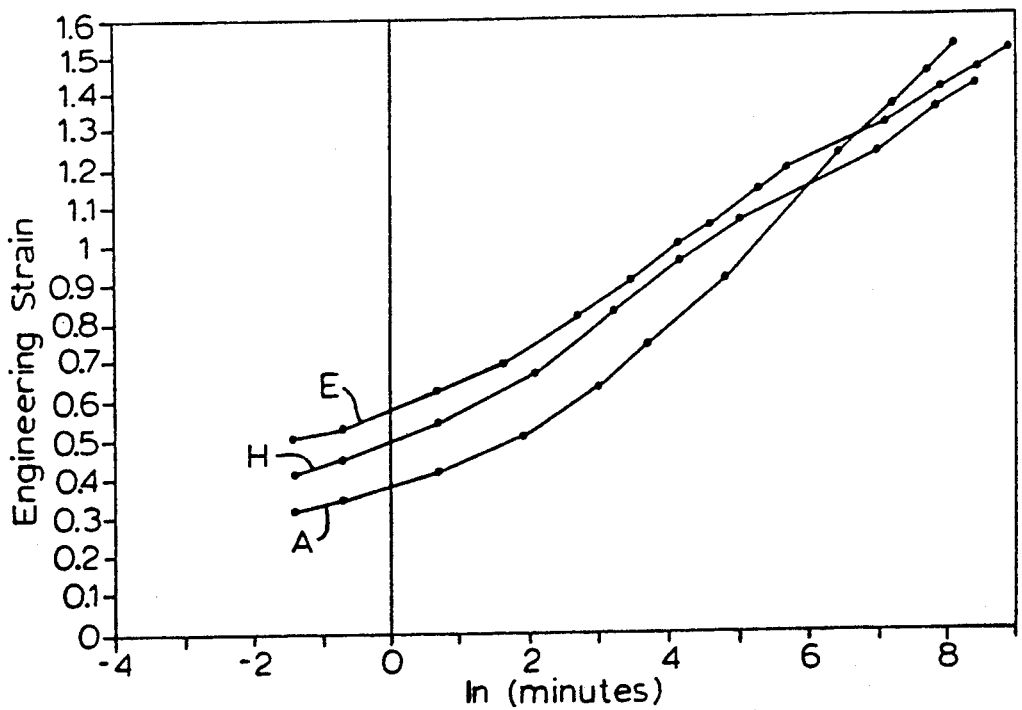
FIG. 8 is a semi-log plot of engineering strain of various Platilon ® films as a function of time, at a loading of 680 psi, wherein A=virgin Platilon ® film, H=heat-treated Platilon ® film, and E=embossed Platilon ® film.
Figure 9:
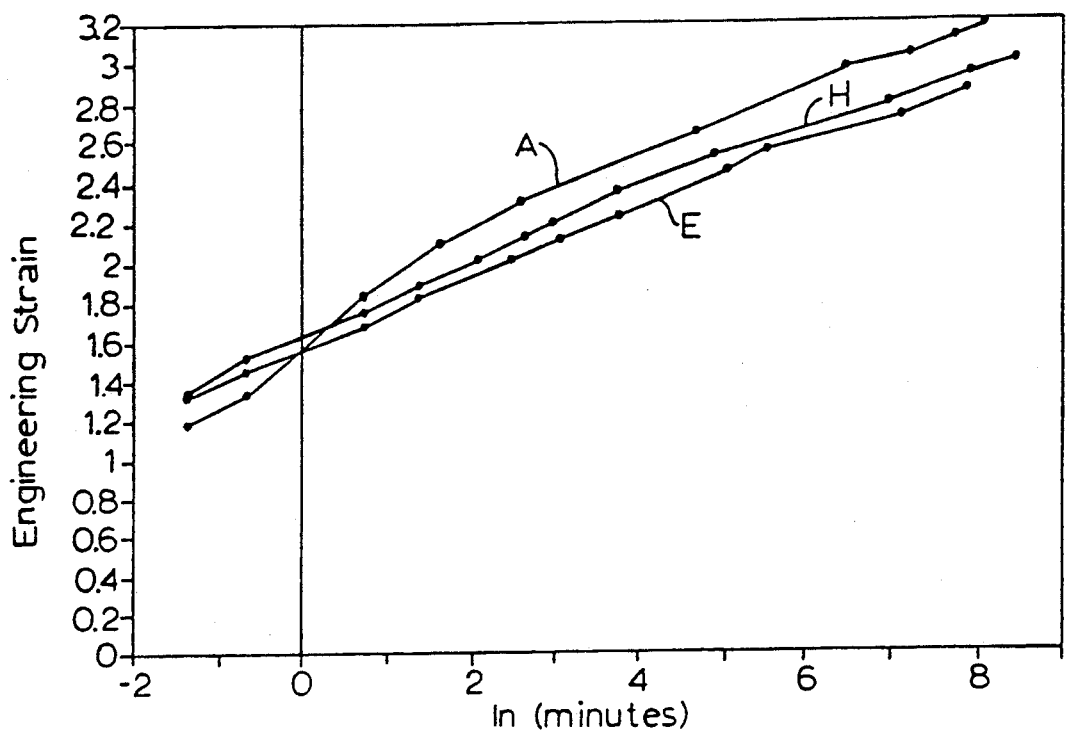
FIG. 9 is a semi-log plot of engineering strain of various Platilon ® films as a function of time, at a loading of 1024 psi, wherein A=virgin Platilon ® film, H=heat-treated Platilon ® film, and E=embossed Platilon ® film.

The data from these tests were also used to plot the semilog graphs of strain as a function of time, at a single loading level, as shown in FIGS. 8 and 9. Specifically, FIG. 8 in a semi-log plot of strain of various Platilon ® films as a function of time, at a loading of 680 psi. FIG. 9 is a semi-log plot of strain of various Platilon ® films as a function of time, at a loading of 1024 psi. In both of FIGS. 8 and 9, "A" denotes virgin Platilon ® film, "H" denotes heat-treated Platilon ® film, and "E" denotes embossed Platilon ® film.

The results in FIG. 8 show that at a loading level of 680 psi, the embossed Platilon ® sample exhibited greater strain than either of the corresponding heat-treated or virgin Platilon ® samples, up to about $10^{6.75}$ minutes, when the strain exhibited by the embossed sample decreased relative to the heat-treated sample, but nonetheless the embossed sample continued to exhibit higher strain than the corresponding virgin Platilon ® sample.

The data in FIG. 9 show that at a loading of 1024 psi, the embossed sample exhibited reduced strain relative to the corresponding heat-treated and virgin samples, beyond the first minute of loading.

Figure 10:
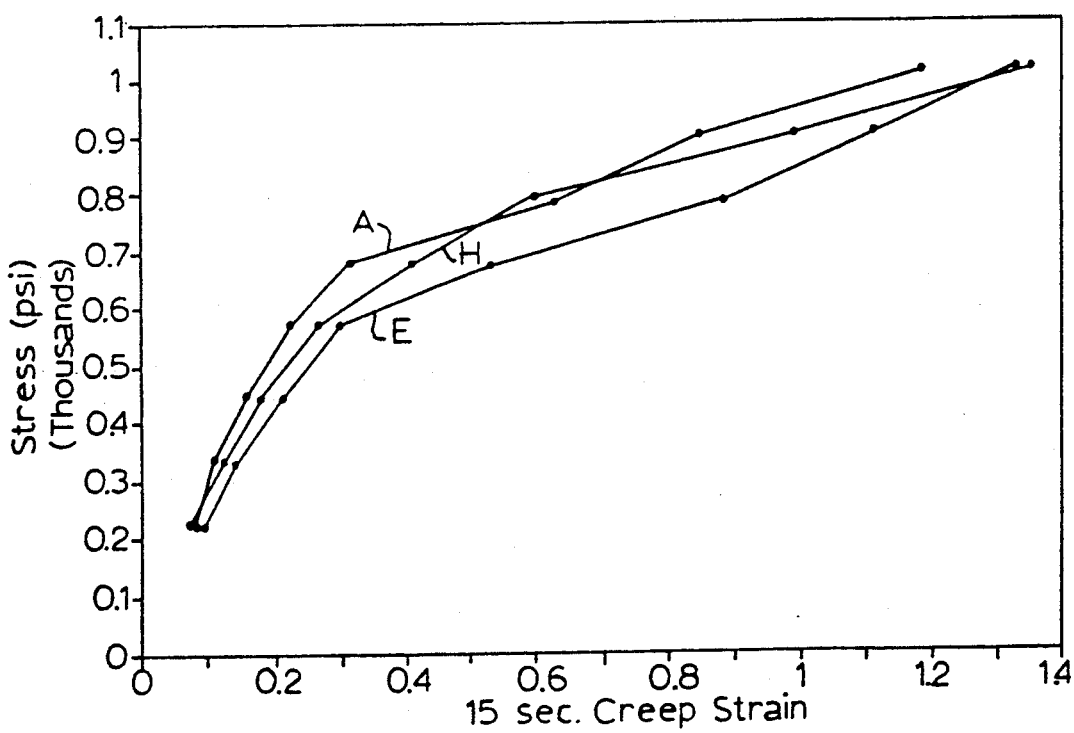
FIG. 10 is a stress-strain plot for various Platilon ® films, measured after 15 seconds of film loading, wherein A=virgin Platilon ® film, H=heat-treated Platilon ® film, and E=

These test data were also employed to generate the graph shown in FIG. 10, which is a stress-strain plot for various Platilon ® films measured after 15 seconds of film loading. Since elastic modulus is measured as the slope of the stress-strain curve, it is seen from FIG. 10 that the embossed material (E) exhibited the lowest modulus of all three samples tested, up to a strain of about 1.28. The lower the elastic modulus, the softer and more stretchable the corresponding film. It therefore is seen that the embossed sample whose stress-strain behavior is shown in FIG. 10 exhibited significantly improved elastic properties relative to the corresponding heat-treated, and virgin, Platilon ® samples.

Figure 11:
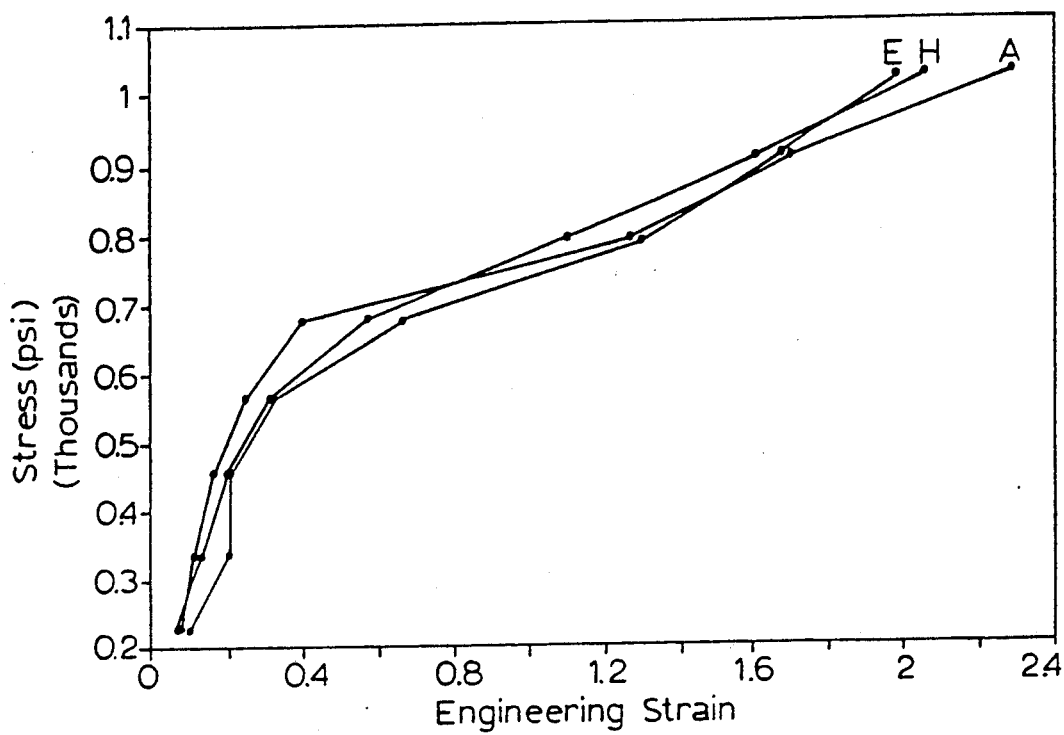
FIG. 11 is a stress-strain plot for various Platilon ® films at a strain rate of 0.2 min$^{-1}$, wherein A=virgin Platilon ® film, H=heat-treated Platilon ® film, and E=embossed Platilon ® film.

The data from the foregoing tests were also employed to produce a stress-strain plot as shown in FIG. 11 for the various Platilon ® films, at a strain rate of 0.2 $min^{-1}$, with the respective virgin, heat-treated, and embossed samples being denoted by the same symbols as in the graphs of the preceding figures. These plotted results show that the embossed sample (E) exhibited the lowest modulus up to a strain of approximately 1.5.

EXAMPLE III

Figure 12:
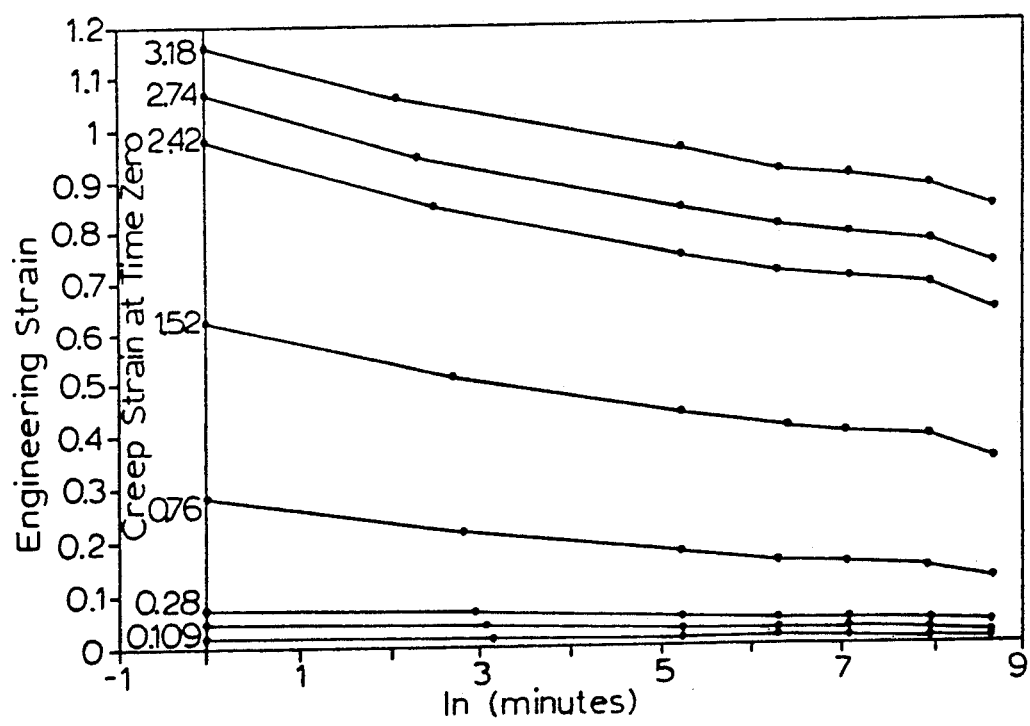
FIG. 12 is a semi-log plot of strain recovery for virgin Platilon ® film as a function of time, with the strain of the previously loaded film at time zero being identified along the vertical axis of the graph.

After the loading tests whose results are shown in FIGS. 5-7 had been carried out for approximately 4,000 minutes, each of the respective loads was replaced with a 5 gram load (to hold the specimen straight so that length measurements could be accurately made). Strain recovery thereafter was monitored, yielding the results which are plotted in the graphs of FIGS. 12, 13, and 14. FIG. 12 is a semi-log plot of strain as a function of time, for virgin Platilon ® film, with the strain of the previously loaded film at time zero being identified along the vertical axis of the graph, and with the various curves corresponding to those shown in the graph of FIG. 5 (i.e., the top curve in FIG. 12 corresponds to a prior loading of 1024 pounds per square inch [wherein the loading has been determined by dividing the load weight by the cross-sectional area of the specimen, the cross-sectional area has been calculated by dividing the sample volume by the specimen length, and the specimen volume has been determined as the specimen weight divided by its density]), with the next lower curve corresponding to a loading of 910 psi, etc.)

Figure 13:
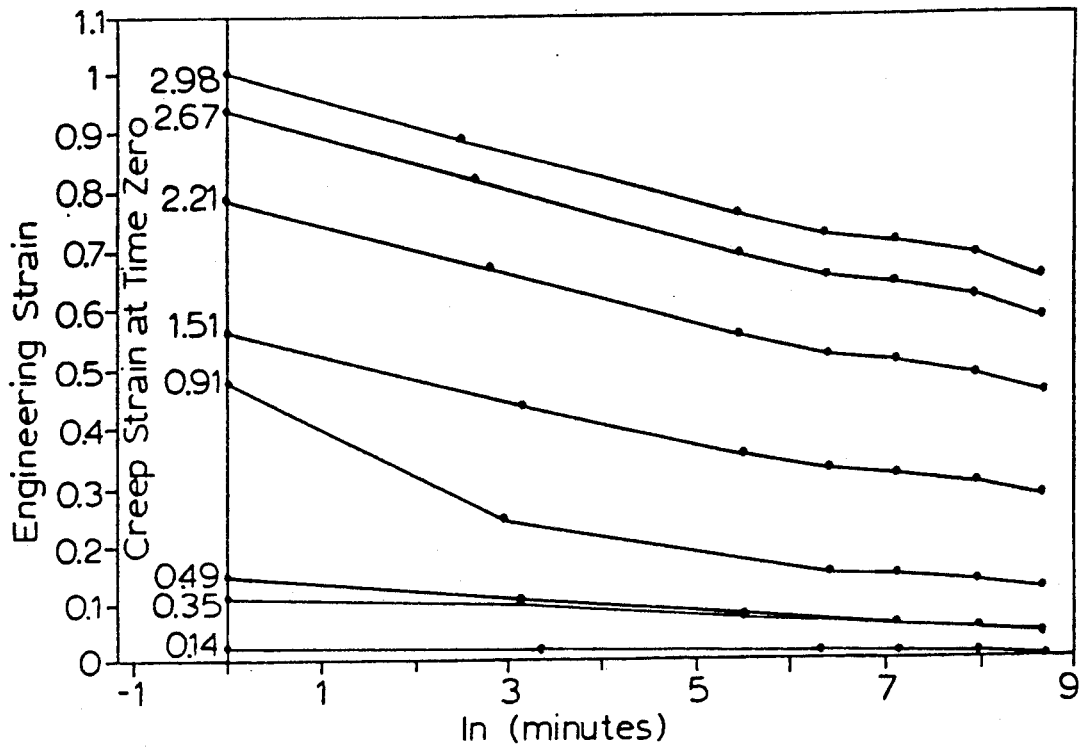
FIG. 13 is a semi-log plot of strain recovery for embossed Platilon ® film as a function of time, with the strain of the previously loaded film at time zero being identified along the vertical axis of the graph.

FIG. 13 shows the corresponding strain recovery plot for embossed Platilon ® film, wherein the curves correspond to the loading curves shown in FIG. 6.

Figure 14:
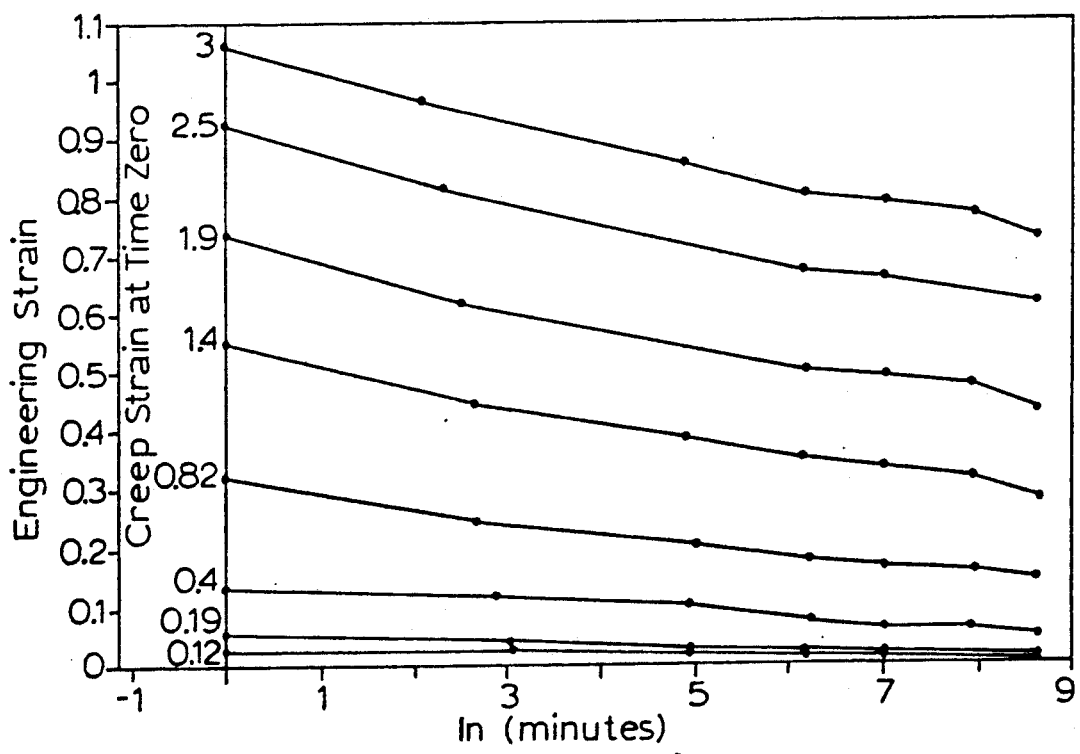
FIG. 14 is a semi-log plot of strain recovery for heat-treated Platilon ® film as a function of time, with the strain of the previously loaded film at time zero being identified along the vertical axis of the graph.

FIG. 14 shows the strain recovery plot for heat-treated Platilon ® film, wherein the curves correspond to the loading curves shown in FIG. 7.

A comparison of the strain recovery graphs of FIGS. 12-14 reveals that the embossed Platilon ® samples exhibit a high rate strain recovery, as compared to corresponding heat-treated, and corresponding virgin, Platilon ® film samples.

Figure 15:
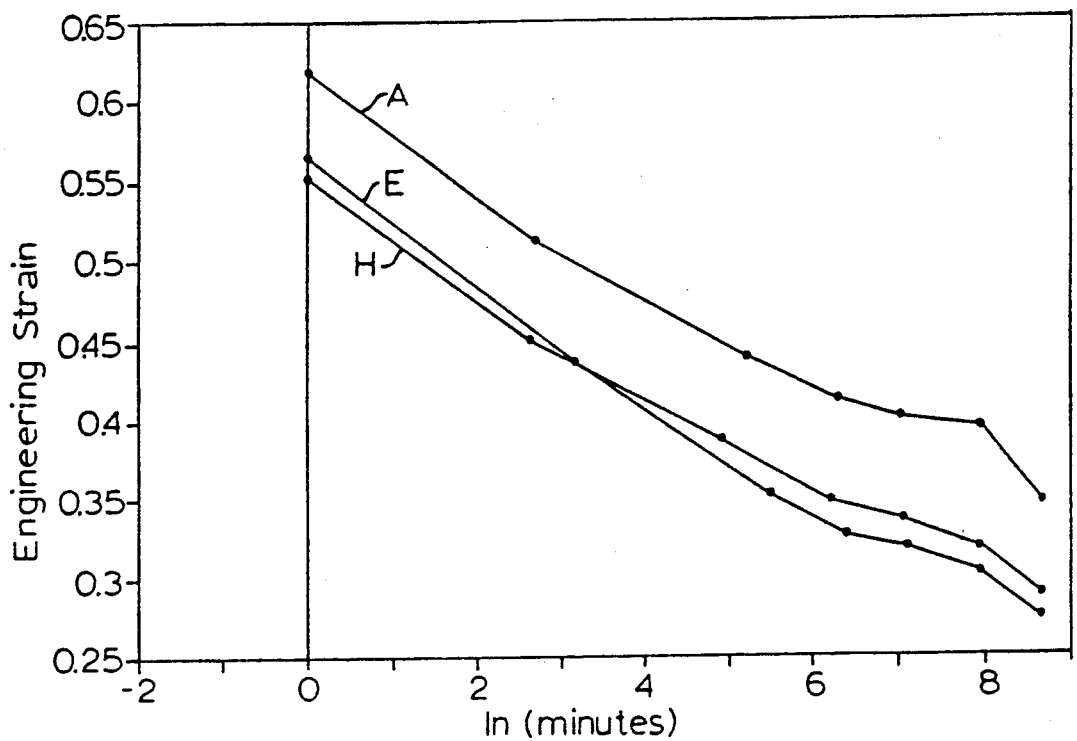
FIG. 15 is a semi-log plot of strain recovery as a function of time, for various Platilon ® films, after loading at 680 psi is discontinued, wherein A=virgin Platilon ® film, H=heat-treated Platilon ® film and E=embossed Platilon ® film.

FIG. 15 is a semi-log plot of strain recovery as a function of time, for various Platilon ® films (denoted as in prior graphs), after film loading at 680 psi, for the samples described in Example II, and corresponding to the strain plot of FIG. 8, in which the strain recovery test was conducted in the same manner employed to generate the graphs of FIGS. 12-14.

The data plotted in FIG. 15 show that the embossed Platilon ® sample exhibited a higher rate of strain recovery than the corresponding heat-treated, or corresponding virgin, Platilon ® samples, and that the overall final recovery of the embossed Platilon ® sample was substantially lower than that of the virgin film, and significantly less than that of the heat-treated film.

EXAMPLE IV

Figure 16:
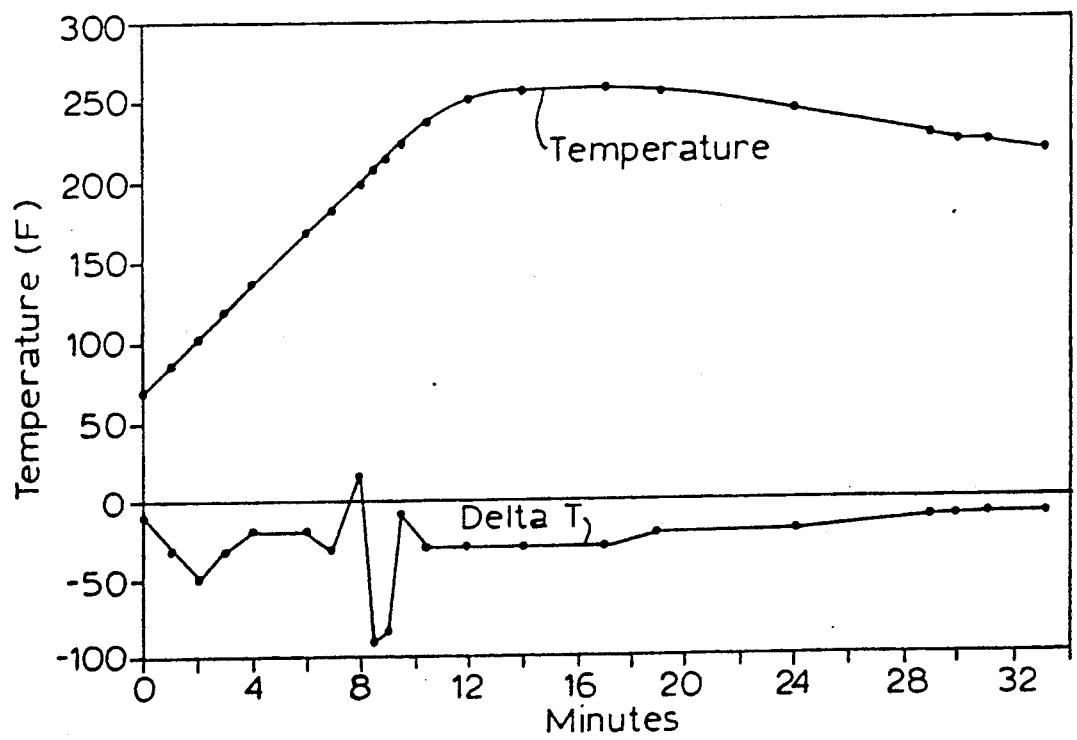
FIG. 16 is a temperature-time plot showing the results of differential thermal analysis testing of virgin Platilon ® film and embossed Platilon ® film.

A differential thermal analysis of virgin and embossed Platilon ® film samples was carried out, utilizing type J thermocouples (Omega Technologies Company, Stamford, Conn.). One thermocouple was wrapped with virgin Platilon ® film, and a second thermocouple was wrapped with an embossed Platilon ® film. The respective thermocouples were placed side-by-side in a hot press between two rubber pads, at a pressure of 400 psi. The platen heaters in the press then were turned on, and the temperatures of the thermocouples were monitored until they reached 200° F., following which heating was discontinued while the thermocouple temperatures continued to be monitored. The upper curve shown in FIG. 16 is a plot of the platen heater temperature as a function of time, and the lower curve represents the differential temperature, $$\text{Delta } T = T_v - T_E$$

wherein:

$T_v$ = temperature of the thermocouple wrapped with virgin platilon ® film; and $T_E$ = temperature of the thermocouple wrapped with embossed Platilon ® film.

Except for a brief period of time at about 8 minutes into the heating operation during which a positive "spike" of the Delta T curve appeared, it is seen that the embossed Platilon ® sample was at a higher temperature than the corresponding virgin Platilon ® sample, including the lower heating range in the vicinity of body temperature (95°-100° F.). Such data show that the embossed polymeric film sample exhibited a higher heat transfer rate than did the corresponding unembossed sample. Such superior heat transfer characteristics of the embossed film provide a corresponding advantage when film of such type is employed in applications such as condoms, where body heat transmissivity is desirably maximized for greater efficacy of the product article.

During a corresponding test in which embossed film was evaluated with heat-treated film in a differential thermal analysis test, no thermal spikes or peaks were present in the corresponding Delta T curve.

EXAMPLE V

The tensile properties of various virgin and embossed polymeric film samples were evaluated by the method of ASTM D412 ("Standard Methods of Tension Testing of Rubber").

The samples which were tested are identified in Table 2 below, with respect to the sample material, average thickness (unembossed), and mesh size of the embossing screen element (if embossed). In the ensuing tests, tensile stress values were based on thickness of the unembossed films, for ease of calculation.

Crosshead speed: 500mm/min
Full scale load: 5 kg
Grip: Pneumatic, Smooth faces

TABLE 2

| Sample | Material | Mesh Size | Average Thickness (mm) |
|---|---|---|---|
| A | PLATILON U073, BASF Elastollan 1185A | — | 0.050 |
| B | PLATILON U073, BASF Elastollan 1185A | 150 | |
| C | PLATILON U073, BASF Elastollan 1185A | 150 | |
| D | PLATILON U073, BASF Elastollan 1185A | 120 | |
| E | PLATILON U073, BASF Elastollan 1185A | 100 | |
| F | PLATILON U073, BASF Elastollan 1185A | — | 0.025 |
| G | PLATILON U073, BASF Elastollan 1185A | 100 | |
| H | PLATILON U073, BASF Elastollan 1185A | 120 | |
| I | PLATILON U073, BASF Elastollan 1185A | 150 | |
| J | PLATILON U073, BASF Elastollan 1185A | | 0.040 |
| K | PLATILON U073, BASF Elastollan 1185A | 100 | |
| L | PLATILON U073, BASF Elastollan 1185A | 120 | |
| M | PLATILON U073, BASF Elastollan 1185A | 150 | |
| X | Majestic Natural Rubber | | 0.068 |
| AA | Pellethane 2363-75A, Bertek 1.5 mils | | 0.038 |
| AB | Pellethane 2363-75A, Bertek 1.5 mils | 100 | |
| BA | Pellethane 2363-75A, Bertek 2.0 mils | | 0.052 |
| BB | Pellethane 2363-75A, Bertek 2.0 mils | 100 | |
| CA | Pellethane 2363-75A, Bertek 2.5 mils | | 0.076 |
| CB | Pellethane 2363-75A, Bertek 2.5 mils | 100 | |
| DA | Pellethane 2363-75A, Bertek 1.5 mils | | 0.038 |
| DB | Pellethane 2363-75A, Bertek 2.0 mils | 100 | |
| EA | Pellethane 2363-75A, Bertek 2.0 mils | | 0.052 |
| EB | Pellethane 2363-75A, Bertek 2.0 mils | 100 | |
| FA | Pellethane 2363-75A, Bertek 2.5 mils | | 0.065 |
| FB | Pellethane 2363-75A, Bertek 2.5 mils | 100 | |
| GA | Kraton KTR-27-G, Shell | | 0.073 |
| GB | Kraton KTR-27-G, Shell | 100 | |

For each sample, five dumbbell-shaped specimens were cut using a standard die oriented with its axis parallel to the extrusion direction of the polymeric film. Specimens were held with powered grips at an air pressure level of 50 psi, and load was applied with an Instron ® testing instrument (Instron Universal Corporation, Canton, Mass.) under the following test conditions:

Gauge width: 7.9 mm
Gauge length: 45mm
Grip face size: 1×1.5 in.

Set out in Table 3 below are data from the tensile strength tests, including mean values for load at break, change of length at break, load at 25% elongation, 25% modulus ($M_{25}$), tensile strength at break, and percent elongation at break, wherein each test parameter was determined for 5 test values (except in a couple of cases, denoted in the table by "*", where only 4 test values were employed).

TABLE 3

| Sample | Load at Break (kg) | Changed Length at Break (mm) | Load at 25% Elongation (kg) | 25% Modulus (kg/cm$^2$) | Tensile Strength at Break (kg/cm$^2$) | % Elongation at Break |
|---|---|---|---|---|---|---|
| A | 1.57 | 229.4 | 0.23 | 58 | 420 | 509.7 |
| B | 2.25 | 302.0 | 0.18 | 47 | 570 | 671.1 |
| C | 0.89 | 183.9 | 0.10 | 26 | 226 | 408.8 |
| D | 2.24 | 294.9 | 0.16 | 39 | 566 | 655.2 |
| E | 1.03 | 299.0 | 0.09 | 22 | 260 | 508.8 |
| F | 1.10 | 268.3 | 0.12 | 57 | 558 | 596.2 |
| G | 0.76 | 231.5 | 0.09 | 45 | 384 | 514.4 |
| H | 0.72 | 239.7 | 0.07 | 34 | 364 | 532.6 |
| I | 0.66 | 233.4 | 0.06 | 31 | 336 | 518.6 |
| J | 1.64 | 259.1 | 0.16 | 49 | 518 | 575.7 |
| K | 1.30 | 242.6 | 0.12 | 39 | 413 | 539.2 |
| L | 1.24 | 250.3 | 0.10 | 33 | 395 | 556.3 |
| M* | 0.98 | 232.6 | 0.09 | 28 | 313 | 516.8 |
| X* | 1.00 | 381.8 | 0.02 | 7 | 219 | 848.4 |
| AA | 1.82 | 260.4 | 0.08 | 20 | 452 | 578.8 |
| AB | 1.97 | 308.0 | 0.05 | 13 | 517 | 684.5 |
| BA | 2.39 | 304.7 | 0.09 | 21 | 582 | 677.2 |
| BB | 2.48 | 330.8 | 0.06 | 16 | 604 | 735.2 |
| CA | 3.47 | 332.8 | 0.11 | 18 | 630 | 771.9 |
| CB | 2.32 | 309.7 | 0.07 | 12 | 386 | 688.3 |
| DA | 1.81 | 284.6 | 0.10 | 34 | 637 | 632.5 |
| DB | 1.11 | 267.1 | 0.03 | 10 | 398 | 593.6 |
| EA | 2.61 | 292.7 | 0.15 | 36 | 588 | 650.4 |
| EB | 1.33 | 248.4 | 0.06 | 15 | 324 | 551.9 |
| FA | 3.58 | 312.4 | 0.18 | 35 | 698 | 694.2 |
| FB | 1.83 | 274.4 | 0.07 | 13 | 356 | 609.7 |
| GA | 1.55 | 317.6 | 0.07 | 12 | 268 | 705.9 |
| GB | 1.73 | 330.0 | 0.06 | 10 | 300 | 733.4 |

EXAMPLE VI

In this test, an unembossed Platilon ® film 50 mm in thickness was evaluated for various mechanical property characteristics, against a corresponding film of the Platilon ® material which was heat-embossed in accordance with the present invention, with a 150 mesh screen as the embossing element. Tensile strength at room temperature and percent ultimate elongation were determined for each of these samples in accordance with the method of ASTM D412. Trouser tear values at 37° C. and at room temperature (RT), at a rate of 5 inches per minute, were measured in accordance with the method of ASTM D1938, for both embossed and unembossed samples. 10%, 20%, and 50% modulus values ($M_{10}$, $M_{20}$, and $M_{50}$, respectively) were determined, for both embossed and unembossed film samples. The results of the various tests are set out in Table 4 below.

TABLE 4

|  | Unembossed | Embossed |
|---|---|---|
| Tensile strength (psi) | 8100 | 9050 |
| % elongation at break | 550 | 590 |
| Trouser Tear (pli) - RT | 400 | 368 |
| Trouser Tear (pli) - 37° C. | 395 | 350 |
| $M_{10}$ | 51 | 33 |
| $M_{20}$ | 116 | 72 |
| $M_{50}$ | 207 | 154 |

As shown by the data in Table 4, the embossed polymeric film exhibited improved tensile strength and percent elongation values as compared to the corresponding unembossed sample. The embossed sample also exhibits substantially reduced modulus values as compared to the corresponding unembossed film.

EXAMPLE VIII

In this example, embossing of various film materials was carried out at different temperature, pressure, and embossing (dwell) time values, to determine preferred values for each of such process conditions.

In these tests, a 10,000 psi hydraulic platen press frame was employed with a standard die set for the embossing of the respective film samples. The platen used in these embossing tests was a 32 square inch platen. The embossing plates were stainless steel wire screens having mesh sizes of 100, 120, and 150.

During the embossing runs, the embossing plate was maintained parallel with the film platen so that equal pressure was applied across the film surface being embossed. The embossing plate was heated by two associated resistance heaters, and temperature was controlled to ±5° F.

As a result of the foregoing tests, the following preferred temperature, pressure, and dwell time conditions were determined for each of the test materials, as shown in Table 5 below.

TABLE 5

| Film Material | Temp. (F.°) | Pressure (psi) | Dwell Time (sec.) |
|---|---|---|---|
| Urethane 75A | 220 | 120 | 10 |
| Urethane 80A | 250 | 120 | 10 |
| Urethane 85A | 250 | 120 | 10 |
| Kraton ® | 190 | 80 | 20 |

Although the foregoing tests employed planar screen elements, it will be appreciated that in commercial practice, textured rollers of appropriate mesh size may be readily fabricated to provide similar embossing patterns, with such rollers being appropriately heatable to facilitate hot embossing, as desired. The provision of such textured rollers is advantageous in effecting high-speed volume production of embossed film in commercial quantities.

Figure 17:
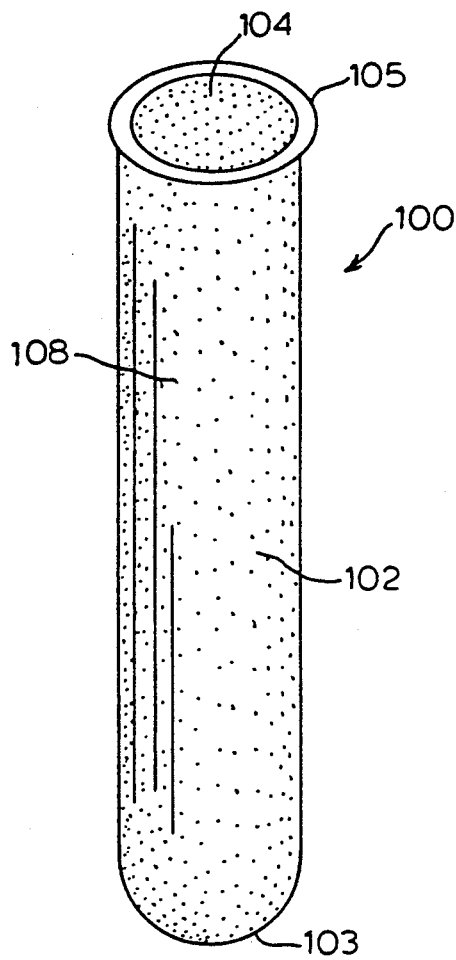
FIG. 17 is a perspective view of a condom article according to one embodiment of the invention, wherein the tubular sheath comprises an embossed thermoplastic elastomeric film.

FIG. 17 is a perspective view of a condom 100 according to one embodiment of the invention, comprising a tubular main sheath portion 102. The tubular mean sheath portion features a closed distal end 103, and an open proximal end 104-which is circumscribingly bounded by an elastic retaining ring 105 of suitable resilient elastic material.

The main sheath portion 102 of the condom 100 may be formed of any suitable elastic material, as for example a thermoplastic elastomeric material selected from the group consisting of polyurethane, polyester, and polyolefin polymers, multiblock rubber-based copolymers, as well as copolymers comprising monomers of the aforementioned polymers, and mixtures, alloys, laminates, and composites thereof. Preferably, the main sheath portion 102 of the condom 100 shown in FIG. 17 is formed of a thermoplastic elastomeric material such as a polyester-based polyurethane material, or a polyether-based polyurethane material.

The exterior surface of the main sheath portion 1.02 of the condom 100 features an embossed pattern 108 thereon comprising a multiplicity of discrete embossments, with a pattern density of from about 1000 to about 100,000 embossments per square inch of embossed surface. As a result of such embossment, the elastic and tactile properties of the condom are substantially enhanced. Such enhancement facilitates the use of elastic materials such as thermoplastic elastomeric films in the fabrication of condoms, where in the absence of embossment the elastic and tactile properties of such polymeric materials may be sufficiently poor to preclude their use in such application.

FIG. 18 is an enlarged view of a portion of an embossed thermoplastic elastomeric film 120, having embossments 122 of triangular shape disposed in a regular array across its surface, over the entire areal extent thereof.

Figure 19:
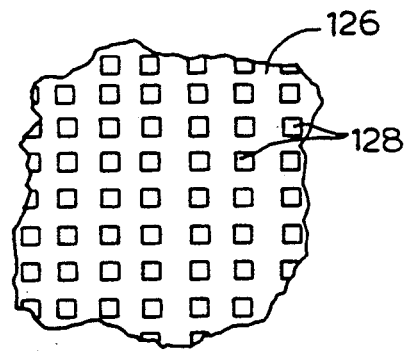
FIG. 19 is an enlarged view of a portion of an embossed thermoplastic elastomeric film having embossments of rectangular shape.

FIG. 19 shows a corresponding enlarged view of a portion of an embossed thermoplastic elastomeric film 126, with embossments 128 of rectangular (square) shape disposed across its surface in a regular array.

Figure 20:
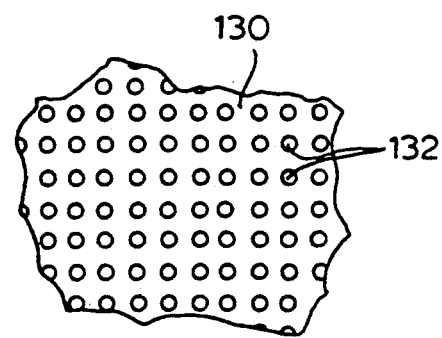
FIG. 20 is an enlarged view of a portion of an embossed thermoplastic elastomeric film having embossments of circular shape.

FIG. 20 shows an enlarged view of a portion of an embossed thermoplastic elastomeric film 130 according to still another embodiment of the invention, featuring embossments 132 of circular shape in a regular array on its surface.

Although it is recognized that condoms are known in the art having protrusions, bumps, knobs, and the like disposed on exterior surfaces thereof, for the ostensible purpose of increasing stimulation of the recipient coital partner, the protrusion elements on such prior art condom products are of a gross dimensional character far exceeding in size the dimensions of the embossments required by the embossment pattern density of the present invention. Further, such prior art condom structures entail protrusion elements which typically are molded or otherwise applied to the base layer of the (latex) condom sheath, and by their nature require increased condom wall thicknesses in the vicinity of such protrusion elements. This increased wall thickness of the prior art "ribbed" or "knobbed" condoms is therefore at odds with the minimum thickness characteristics generally desired for the condom sheath, in addition to complicating the manufacture of the condom article.

It thus is seen that the provision of embossed or textured films in the manufacture of condoms according to the present invention achieves a substantial advance in the art. Specifically, the invention renders various film and sheet materials significantly more useful for production of condoms, thereby facilitating low-cost mass production of condoms using economical and readily available polymeric film materials.

While the foregoing discussion has been directed primarily to condoms as product articles in which embossed or textured film of the present invention may usefully be employed, it will be appreciated that the utility of the invention is not limited, but rather extends to any other end use applications in which film or sheet materials may advantageously be employed.

Further, while the invention has been described herein with specific reference to preferred aspects, features, and embodiments, it will be appreciated that numerous variations, modifications, and other embodiments are possible. Accordingly, all such variations, modifications and embodiments are to be regarded as being within the spirit and scope of the invention.

What is claimed is:

1. An imperforate, uniform thickness elastic film having an embossed pattern thereon comprising a multiplicity of discrete embossments in a regular array, wherein the embossments are all of a similar shape and configuration, and are in spaced-apart relationship to one another in the array, with a pattern density of from about 1000 to about 100,000 embossments per square inch of embossed surface.

2. A film according to claim 1, comprising a thermoplastic elastomeric film.

3. A film according to claim 1, whose thickness does not exceed about 100 mils.

4. A film according to claim 1, whose thickness does not exceed about 40 mils.

5. A film according to claim 1, whose thickness is in the range of from about 1 to about 10 mils.

6. A film according to claim 1, whose pattern density is from about 2000 to about 50,000 embossments per square inch of embossed surface.

7. A film according to claim 1, whose pattern density is from about 5000 to about 40,000 embossments per square inch of embossed surface.

8. A film according to claim 1, whose pattern density is from about 10,000 to about 30,000 embossments per square inch of embossed surface.

9. A film according to claim 1, comprising polyurethane film.

10. A film according to claim 1, comprising polyester polyurethane film.

11. A film according to claim 1, wherein the embossed pattern is formed by elevated heat and/or pressure forming conditions.

12. A film according to claim 1, characterized by a reduced elastic modulus as compared to a corresponding unembossed film.

13. A film according to claim 1, whose embossed pattern has been formed by contacting the film with a foraminous element at elevated heat and/or pressure conditions.

14. A film according to claim 1, whose embossed pattern has been formed by embossing elements, comprising a first, relatively harder foraminous element, and a second, relatively softer, deformable and resilient element matable with the first element, with the film therebetween under elevated temperature and/or pressure conditions imparting the embossed pattern to the film.

15. A film according to claim 1, comprising embossments with a triangular shape.

16. A film according to claim, comprising embossments with a polygonal shape.

17. A film according to claim, comprising embossments with a quadrilateral shape.

18. A film according to claim 1, comprising embossments with a circular shape.

19. A condom comprising an elastic film according to claim 1.

20. A condom comprising a generally tubular main sheath portion comprising a film according to claim 1.

21. A film according to claim 1, which is devoid of ribs.

22. An imperforate, uniform thickness elastic film having an embossed pattern thereon comprising a multiplicity of discrete embossments in a regular array, wherein the embossments are all of a similar shape and configuration, and are in spaced-apart relationship to one another in the array, with a pattern density of from about 1000 to about 100,000 embossments per square inch of embossed surface, wherein the 10% modulus ($M_{10}$) and 20% modulus ($M_{20}$) values are at least 30% less, and whose 50% modulus ($M_{50}$) value is at least 20% less, than corresponding moduli values for a corresponding unembossed film, and whose tensile strength as measured by the method of ASTM D412 is at least 10% greater than the tensile strength measured by said method for a corresponding unembossed film.

* * * * *

UNITED STATES PATENT AND TRADEMARK OFFICE
CERTIFICATE OF CORRECTION

PATENT NO. : 5,098,755

DATED : March 24, 1992

INVENTOR(S) : ALBERT C. TANQUARY, ET AL.

It is certified that error appears in the above-identified patent and that said Letters Patent is hereby corrected as shown below:

In Column 1, after the title, insert

-- GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein. --

Signed and Sealed this

Twenty-second Day of November, 1994

*Attest:*

BRUCE LEHMAN

*Attesting Officer*    *Commissioner of Patents and Trademarks*